United States Patent [19]

Lacombe et al.

[11] Patent Number: 5,698,830
[45] Date of Patent: Dec. 16, 1997

[54] PROCESS FOR THE PREPARATION OF ALKANESULPHONIC ACIDS

[75] Inventors: Sylvie Lacombe, Artiguelouve; Jean Ollivier, Arudy, both of France

[73] Assignee: Elf Atochem S.A., France

[21] Appl. No.: 605,333

[22] Filed: Feb. 21, 1996

Related U.S. Application Data

[63] Continuation of Ser. No. 253,021, Jun. 2, 1994, abandoned.

[30] Foreign Application Priority Data

Jun. 2, 1993 [FR] France ................................. 93 06560

[51] Int. Cl.⁶ .................................................. C07B 33/00
[52] U.S. Cl. .................. 204/157.15; 204/157.41; 204/157.49; 204/157.5; 204/157.52; 204/157.6; 204/157.76; 204/157.78
[58] Field of Search ............................ 204/157.4, 157.41, 204/157.49, 157.5, 157.52, 157.6, 157.76, 157.78

[56] References Cited

U.S. PATENT DOCUMENTS

| | | | |
|---|---|---|---|
| 2,697,722 | 12/1954 | Johnson et al. | 260/513 |
| 3,336,210 | 8/1967 | Furrow | 204/157.78 |
| 3,337,437 | 8/1967 | Furrow et al. | 204/157.78 |
| 3,392,095 | 7/1968 | Dimond et al. | 204/157.78 |
| 3,457,155 | 7/1969 | Rosinger | 204/157.78 |
| 4,643,813 | 2/1987 | Sato et al. | 204/157.78 |

OTHER PUBLICATIONS

J. Org. Chem. vol. 37, No. 22, 1972, R.W. Murray, et al., "Photosensitised oxidation of dialkly disulphides" p. 3519 Table I.

Murray et al., "Photosensitized Oxidation of Dialkyl disulfides." *J. Org. Chem.*, vol. 37, No. 22 1972, pp. 3516–3520.

*Primary Examiner*—Cecilia Tsang
*Assistant Examiner*—C. Delacroix-Muirheid
*Attorney, Agent, or Firm*—Bell, Boyd & Lloyd

[57] ABSTRACT

The invention relates to the preparation of alkanesulphonic acids by photo-oxidation of dialkyl disulphides.

The procedure is carried out in solution in an alcohol using a light source irradiating between 200 and 320 nm.

11 Claims, No Drawings

PROCESS FOR THE PREPARATION OF ALKANESULPHONIC ACIDS

This is a continuation of application Ser. No. 08/253,021, filed Jun. 2, 1994, now abandoned.

FIELD OF THE INVENTION

The present invention relates to the synthesis of alkanesulphonic acids and its subject is, more particularly, the preparation of these acids from the corresponding dialkyl disulphides.

BACKGROUND OF THE INVENTION

The alkanesulphonic acids and their salts have numerous industrial applications, especially as detergents, emulsifiers, esterification catalysts and hardeners for some resins.

Industrially, alkanesulphonic acids are most often produced from alkanes by sulpho-oxidation or by sulphochlorination. These two routes of synthesis have, however, the inconvenience of leading to the formation of products which are sulphonated on the various carbon atoms of the hydrocarbon chain. Moreover, the hydrolysis of alkanesulphonyl chlorides generally leads to alkanesulphonic acids which are more or less intensely colored, requiring a final decolorizing treatment, for example by means of chlorine.

In the last few years much work has been devoted to the atmospheric photochemistry of sulphur-containing organic compounds (thiols, sulphides and disulphides) which are, in trace amounts, atmospheric constituents of biogenic origin or, more often, pollutants arising from energy production technologies. Most of these photochemical studies were carried out in the gas phase at low pressure ($\leq 1$ atm) in the presence of air, oxygen, an eluent gas and sometimes nitrogen oxides. All the results obtained mention the formation of sulphur dioxide and sulphonic and sulphuric acids, as well as other products which vary according to the conditions employed.

Research into solution photo-oxidation of sulphur-containing organic compounds has almost exclusively been devoted to the photo-oxidation of sulphides in the presence of photosensitizers for the preparation of sulphoxides and sulphones. Only one article (R. W. MURRAY et al., J. Org. Chem. Soc., 37, 1972, p. 3516) relates to the formation of thiosulphinates by photo-oxidation of disulphides in the presence of methylene blue as photosensitizer.

DESCRIPTION OF THE INVENTION

It has now been found that excellent yields of alkanesulphonic acids may be obtained by photo-oxidation of dialkyl disulphides in the presence of oxygen without a catalyst if the procedure is carried out in solution in an alcohol with a light source irradiating between 200 and 320 nm. This process, which uses the following reaction:

has the additional advantage of leading to acids for which the sulphonic group is exclusively attached to the end of the hydrocarbon chain.

The subject of the invention is thus a process for the preparation of an alkanesulphonic acid R—$SO_3H$ from the corresponding dialkyl disulphide R—S—S—R, characterized in that it consists in submitting an alcoholic solution of the dialkyl disulphide, in the presence of oxygen, to an irradiation by light rays of wavelength between 200 and 320 nm.

The process according to the invention may be applied to the synthesis of alkanesulphonic acids for which the hydrocarbon chain, which may be linear or branched, may contain from 1 to 16 carbon atoms, in particular from 1 to 4 carbon atoms. Dimethyl disulphide, diethyl disulphide, dipropyl disulphide and dibutyl disulphide may be mentioned as examples of dialkyl disulphides to use as starting products.

The alcohol used may advantageously be chosen from primary, secondary or tertiary alcohols containing from 1 to 12 carbon atoms. However, it is preferred to use a $C_1$ to $C_4$ alcohol and, more particularly, methanol. The dialkyl disulphide content of the starting alcoholic solution may vary within wide limits depending on the alcohol and the disulphide used. It may generally range from 0.1 to 90% by weight, but is preferably between 2 and 25%.

Oxygen, which is necessary for the reaction, may be provided in pure form or diluted by an inert gas such as, for example, nitrogen. The oxygen is preferably introduced gradually into the alcoholic solution. The total amount of oxygen needed is at least 4 moles per mole of dialkyl disulphide present in the initial solution, but it is preferred to carry out the procedure with an oxygen excess of at least 50%.

The photo-oxidation according to the invention may be conducted at a temperature between $-20°$ C. and the boiling point of the alcohol, but the procedure is preferably carried out between 18 and $45°$ C. The operation is advantageously performed at atmospheric pressure, but it would not be departing from the scope of the present invention to work under a slight pressure.

The process according to the invention may be implemented in a batchwise or continuous manner, in any photochemical reactor, for example in an immersion or a falling-film reactor fitted with one or more low, medium or high pressure mercury vapor lamps or excimer lamps emitting in the ultraviolet region.

EXAMPLES

The examples which follow illustrate the invention without, however, any limitation being implied.

EXAMPLE 1 a) A photochemical reactor fitted with a central immersion lamp holder is used. The light source is a 450 W medium pressure mercury Hanovia lamp (reference 679 A) and the lamp holder used is made of quartz. With this lamp holder, the volume of liquid in the reactor is 300 ml and the light path is 10 mm. The reactor and the lamp holder are thermostatted by two independent cold groups ($15°$ C. for the reactor and for the lamp holder). Oxygen is introduced at atmospheric pressure via the base of the reactor through a slnter (porosity 4). To minimize entrainment of volatile products the gaseous effluent at the reactor outlet passes through a condenser which is cooled to $-20°$ C.; it is then admitted into a bubbler containing sodium hydroxide and finally directed towards a flare.

300 ml of a 0.56M dimethyl disulphide (DMDS) solution in methanol (equivalent to 0.168 mol of DMDS) are introduced into the reactor and the solution is then left over an oxygen sparge (flow rate: 1 liter/hour) hour) for 2 hours at $10°$ C. The lamp is then lit and, while maintaining the oxygen sparge (2 l/h), irradiation is carried out for 14 hours at $35°$–$40°$ C.

After this period, the solution is clear and homogeneous and no precipitate is found to be present. After evaporation of the solvent, a colorless liquid is obtained for which the $^1$H NMR analysis indicates almost complete conversion (99%) Of the DMDS with a methanesulphonic acid (MSA) yield of 65%.

The main side product of the reaction is sulphuric acid (SA) (yield 18%) which is partially esterified in the methanol to give the methyl hydrogen ester (MHSA). Among the side products detected in low quantity, methanesulphonic acid methyl ester (MMS:=2%), dimethyl sulphone ($DMSO_2$: 0.6%) and traces of methanesulphinic acid methyl ester (MMSI) are found to be present, but it is noted that methyl methanethiosulphonate (MMTS) is absent.

b) The procedure is carried out as above, but replacing the methanolic solution by pure DMDS (300 ml). Irradiation in the presence of oxygen rapidly leads to the production of an inhomogeneous and opalescent liquid, making it necessary to stop the operation at the end of 2 hours. Only traces of MSA are present in the heavy phase separated off after settling has taken place. Analysis of the volatile effluents indicates formation of sulphur dioxide, methane and methanethiol.

COMPARATIVE EXAMPLES 2 to 4

The operation is repeated as in Example 1a, but replacing the methanol by cyclohexane (Example 2) or acetonitrile (Example 3) or by using a lamp holder made of Pyrex (Example 4). With this lamp holder, the volume of liquid in the reactor is 200 ml and the light path is 8 mm.

The results obtained in these tests are collected in the following table along with those of Example 1a for comparison.

| EXAMPLE | 1a | 2 | 3 | 4 |
|---|---|---|---|---|
| Operating conditions | | | | |
| Solvent | Methanol | Cyclohexane | Acetonitrile | Methanol |
| Initial concentration of DMDS | 0.56 M | 0.56 M | 0.56 M | 0.49 M |
| Lamp holder | Quartz | Quartz | Quartz | Pyrex |
| Irradiation time (h) | 14 | 11.5 | 5.25 | 9.5 |
| Results: | | | | |
| Degree of conversion of DMDS (%) | 99 | 50 | 40 | 21 |
| Yield (%) of: | | | | |
| MSA | 65 | 4 | 5.7 | 7.1 |
| MMS | 2 | — | — | trace |
| DMSO | 0.6 | — | — | trace |
| MMSI | trace | — | — | trace |
| SA + MHSA | 18 | 0.3 | 0.3 | Not determined |
| MMTS | 0 | 1.2 | 5.6 | 6.2 |

Examination of the results makes it possible to appreciate the importance of the solvent and the filter used for the degree of conversion of the DMDS, the yield of MSA and the undesirable formation of MMTS. Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of an alkanesulphonic acid from the corresponding dialkyl disulphide, consisting of submitting a $C_1$ to $C_3$ alcoholic solution of the dialkyl disulphide, with oxygen, to an irradiation by light rays of wavelength between 200 and 320 nm.

2. Process according to claim 1, wherein the alkyl radicals of the dialkyl disulphide are linear or branched alkyl radicals containing from 1 to 16, preferably from 1 to 4 carbon atoms.

3. Process according to claim 2, wherein the alkyl radical contains 1 to 4 carbon atoms.

4. Process according to claim 1, wherein the dialkyl disulphide content of the starting alcoholic solution is between 0.1 and 90% by weight.

5. Process according to claim 4, wherein the dialkyl disulphide content of the starting alcoholic solution is between 1 and 25% by weight.

6. Process according to claim 1, wherein the procedure is carried out at a temperature between −20° C. and the boiling point of the alcohol.

7. Process according to claim 6, wherein the temperature is between 18° and 45° C.

8. Process according to claim 1, wherein the procedure is carried out at atmospheric pressure.

9. Method for the synthesis of methanesulphonic acid from dimethyl disulphide comprising the process of claim 1.

10. Process according to claim 1, wherein the alcoholic solution is methanol.

11. Process for the preparation of alkanesulphonic acid from the corresponding dialkyl disulphide, consisting of submitting a $C_1$ to $C_3$ alcoholic solution of the dialkyl disulphide, with oxygen, to an irradiation by light rays of wavelength between 200 and 320 nm; wherein the dialkyl disulphide content of the starting alcoholic solution is between 1 and 25% weight; and wherein the procedure is carried out at a temperature between 18° C. and 45° C., and at atmospheric pressure.

* * * * *